(12) United States Patent
Hosokai

(10) Patent No.: US 12,582,304 B2
(45) Date of Patent: Mar. 24, 2026

(54) ELECTRONIC COMPONENT HOLDING MEMBER AND ENDOSCOPE

(71) Applicant: OLYMPUS MEDICAL SYSTEMS CORP., Tokyo (JP)

(72) Inventor: Shigeru Hosokai, Hachioji (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 360 days.

(21) Appl. No.: 18/515,720

(22) Filed: Nov. 21, 2023

(65) Prior Publication Data

US 2024/0081631 A1 Mar. 14, 2024

Related U.S. Application Data

(63) Continuation of application No. PCT/JP2021/032168, filed on Sep. 1, 2021.

(51) Int. Cl.
*A61B 1/05* (2006.01)
*H05K 1/02* (2006.01)

(52) U.S. Cl.
CPC ........... *A61B 1/051* (2013.01); *H05K 1/0284* (2013.01)

(58) Field of Classification Search
CPC ......... A61B 1/05; A61B 1/0011; A61B 1/051; H04N 23/555; H05K 1/0284
USPC ........................................................ 174/255
See application file for complete search history.

(56) References Cited

U.S. PATENT DOCUMENTS

| | | |
|---|---|---|
| 2009/0002973 A1 | 1/2009 | Watanabe et al. |
| 2015/0029570 A1 | 1/2015 | Ito et al. |
| 2017/0127921 A1 | 5/2017 | Motohara et al. |

FOREIGN PATENT DOCUMENTS

| | | |
|---|---|---|
| EP | 3 231 350 A1 | 10/2017 |
| JP | 2004-077382 A | 3/2004 |
| JP | 4055028 B2 | 3/2008 |
| JP | 2013-180078 A | 9/2013 |
| JP | 2014-183520 A | 9/2014 |
| JP | 2018-068667 A | 5/2018 |
| WO | 2007/058096 A1 | 5/2007 |
| WO | 2016/092986 A1 | 6/2016 |

OTHER PUBLICATIONS

International Search Report dated Oct. 5, 2021 received in PCT/JP2021/032168.

*Primary Examiner* — Tremesha W Burns
(74) *Attorney, Agent, or Firm* — Scully, Scott, Murphy & Presser, P.C.

(57) ABSTRACT

An electronic component holding member includes a first base material including an electronic component, a first resin molded product, and first metal patterns in which a signal pattern and a grounding pattern are formed on a non-planar surface, a second base material including a second resin molded product, and a second metal pattern formed on a non-planar surface so as to overlap at least part of the first metal patterns, and grounding wiring configured to connect the grounding pattern and the second metal pattern.

10 Claims, 12 Drawing Sheets

ELECTRONIC COMPONENT HOLDING MEMBER AND ENDOSCOPE

CROSS REFERENCE TO RELATED APPLICATION

This application is a continuation application of PCT/JP2021/032168 filed on Sep. 1, 2021, the entire contents of which are incorporated herein by this reference.

BACKGROUND OF THE INVENTION

1. Field of the Invention

The present invention relates to an electronic component holding member that holds an electronic component in a resin molded product, and an endoscope equipped with the electronic component holding member.

2. Description of the Related Art

Conventionally, an electronic component holding member that holds an electronic component in a resin molded product has been proposed and commercialized.

For example, Japanese Patent No. 4055028 describes the following technique. Circuit wiring is formed on a film resin, a groove in which the circuit wiring is stored is formed on a metal base to sandwich and shield the film resin between the metal base and another metal lid. An antenna is formed on a back surface of the metal base, and the millimeter wave antenna and a processing unit are integrated. Another resin film is superimposed and clamped on the member formed in this manner, thereby realizing a microstrip line similar to an ordinary printed wiring board. Here, the microstrip line has, for example, a structure in which a linear conductor foil is formed on a surface of a plate-shaped dielectric substrate having a conductor foil formed on a back surface, and is a transmission path that transmits an electromagnetic wave.

SUMMARY OF THE INVENTION

An electronic component holding member according to one aspect of the present invention includes a first base material including an electronic component, a first resin molded product configured to hold the electronic component, and first metal patterns formed on a surface including a non-planar surface, of the first resin molded product, the first metal patterns including a signal pattern configured to perform signal transmission with the electronic component, and a grounding pattern, a second base material including a second resin molded product disposed on the first base material, and a second metal pattern formed on a surface including a non-planar surface, of the second resin molded product so as to overlap at least part of the first metal patterns with the second resin molded product between the second metal pattern and the at least part of the first metal patterns, and grounding wiring configured to connect the grounding pattern and the second metal pattern.

An endoscope according to one aspect of the present invention is equipped with an electronic component holding member including a first base material including an electronic component, a first resin molded product configured to hold the electronic component, and first metal patterns formed on a surface including a non-planar surface, of the first resin molded product, the first metal patterns including a signal pattern configured to perform signal transmission with the electronic component, and a grounding pattern, a second base material including a second resin molded product disposed on the first base material, and a second metal pattern formed on a surface including a non-planar surface, of the second resin molded product so as to overlap at least part of the first metal patterns with the second resin molded product between the second metal pattern and the at least part of the first metal patterns, and grounding wiring configured to connect the grounding pattern and the second metal pattern.

DETAILED DESCRIPTION OF THE PREFERRED EMBODIMENTS

Hereinafter, embodiments of the present invention will be described with reference to the drawings. However, the present invention is not limited by the embodiments described below.

Note that in the description of the drawings, same or corresponding elements are assigned with same reference signs as appropriate. It should also be noted that the drawings are schematic and that, within one drawing, the relationships of the lengths of respective elements, the ratios of the lengths of the respective elements, the quantities of the respective elements and the like may differ from reality to simplify explanation. Further, among the plurality of drawings, parts where the relationships and ratios of mutual lengths are different may be included.

First Embodiment

Figure 1:
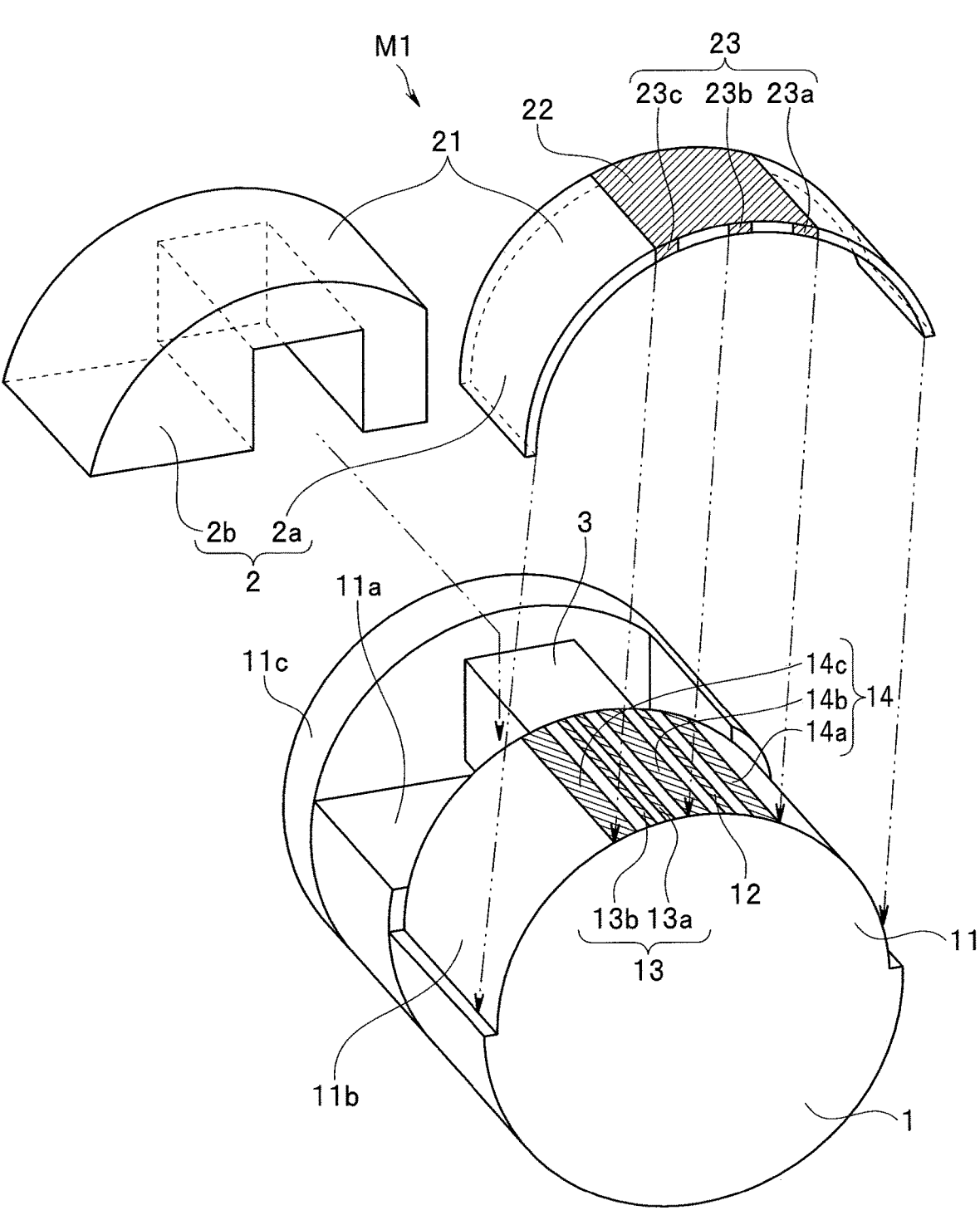
FIG. 1 is a perspective view showing a first base material and a second base material that are disassembled in an electronic component holding member of a first embodiment of the present invention.
Figure 2:
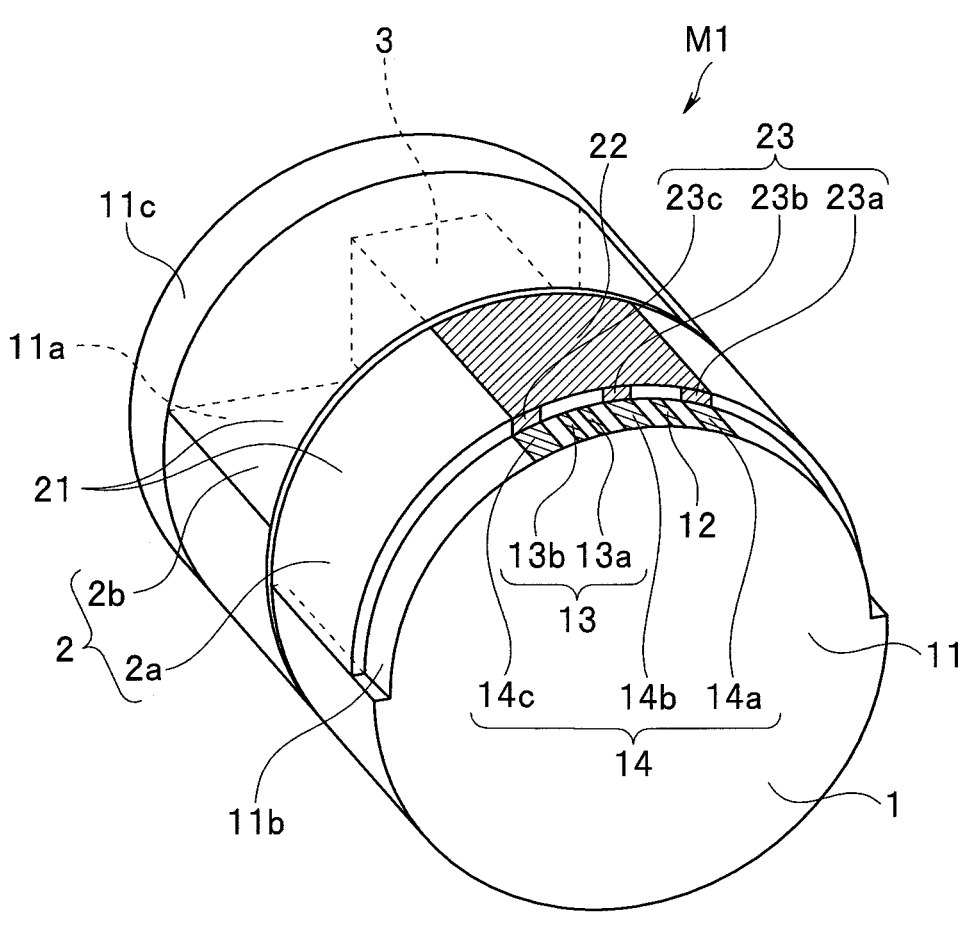
FIG. 2 is a perspective view showing the electronic component holding member of the above-described first embodiment.

FIG. 1 to FIG. 4 show a first embodiment of the present invention. FIG. 1 is a perspective view showing a first base material 1 and a second base material 2 that are disassembled in an electronic component holding member M1. FIG. 2 is a perspective view showing the electronic component holding member M1.

The electronic component holding member M1 includes the first base material 1 and the second base material 2. The first base material 1 and the second base material 2 are molded components formed by an MID (molded interconnect devices) technique. The MID means a three-dimensionally molded circuit component in which wiring for electric circuit is integrally formed on a surface of a three-dimensional molded product such as an injection molded product. By using the MID technique, circuit wiring can also be formed on inclined surfaces, vertical surfaces, curved surfaces, through-holes inside molded bodies and the like, unlike conventional two-dimensional circuits.

In the present embodiment, for example, an MID technique is used once to form the first base material 1, and a second MID technique is used for the first base material 1 to dispose the second base material 2 on the first base material 1. However, regardless of this, the second base material 2 may be formed on the first base material 1 by the MID technique of a two-color-molding type.

Accordingly, a first resin molded product 11 configuring the first base material 1, and a second resin molded product 21 configuring the second base material 2 may be formed of the same resin material, or may be formed of different resin materials. Hereinafter, the MID technique used twice in the present embodiment, and the MID technique of two-color-molding type are collectively referred to as two-stage MID.

The first base material 1 has an electronic component, the first resin molded product 11 holding the electronic component, and first metal patterns formed on a surface including a non-planar surface, of the first resin molded product 11.

The electronic component of the present embodiment is, for example, a front-view type image pickup module 3 (image pickup unit) including an image pickup device. The image pickup module 3 is modularized by integrally bonding an image pickup optical system to the image pickup device, for example.

The first resin molded product 11 is a component formed in a three-dimensional shape by injection molding in which a resin material containing a metal catalyst is heated and softened, and injection pressure is applied to the resin material to press and fill the resin material into a first molding die. The first resin molded product 11 of the present embodiment is formed into a generally cylindrical shape as a whole and has an L-shaped cutout 11*a* for accommodating the image pickup module 3, a semicircular recessed step portion 11*b* formed on a proximal end side of the L-shaped cutout 11*a*, and a disk-shaped portion 11*c* formed on a distal end side of the L-shaped cutout 11*a*. The first metal pattern is formed on a surface including a cylindrical surface (non-planar surface) of the semicircular recessed step portion 11*b*.

The surface of the molded first resin molded product 11 is irradiated with laser light to perform patterning and activation of the metal catalyst, electroless plating is applied to metallize only an activated portion (providing nickel plating on copper plating, for example) to form the first metal patterns. The first metal patterns in the present embodiment includes signal patterns 12 and 13 that perform signal transmission with the image pickup module 3, and a grounding pattern 14. Note that in the following, the signal patterns 12 and 13 and the grounding pattern 14 are collectively referred to as first metal patterns 12, 13 and 14 as appropriate.

In the illustrated example, the signal pattern 12 is a single-wire pattern, and the signal pattern 13 is a double-wire pattern and includes a first pattern 13*a* and a second pattern 13*b*. The signal pattern 12 is used to transmit a single end signal, for example. The signal pattern 13 is used to transmit a differential signal, for example. Note that here, one signal pattern 12 and a pair of signal patterns 13 are illustrated for simplification, but in reality, for example, a plurality of signal patterns 12 and a plurality of pairs of signal patterns 13 are provided, and grounding patterns 14 are provided among the plurality of signal patterns 12 and the plurality of pairs of signal patterns 13. In other embodiments described hereinafter, same simplification or further simplification is performed.

The first metal patterns 12, 13, and 14 are provided to extend into the L-shaped cutout 11*a* from the semicircular recessed step portion 11*b*, and the image pickup module 3 is installed onto a land (not illustrated) provided at end portions of the first metal patterns 12, 13 and 14. Accordingly, the first resin molded product 11 holds the image pickup module 3. Note that in the disk-shaped portion 11*c*, a hole is provided, and light from a subject is incident on the image pickup module 3 through the hole.

The first base material 1 where the first metal patterns 12, 13 and 14 are formed and the image pickup module 3 is installed is put in a second molding die, and the second resin molded product 21 is injection-molded. As for the injection molding of the second resin molded product 21, a resin material containing a metal catalyst is heated and softened, injection pressure is applied to the resin material to press the resin material into the second molding die to fill the L-shaped cutout 11*a* and the semicircular recessed step portion 11*b*, whereby the resin material is molded in a three-dimensional shape.

The first base material 1 on which the second resin molded product 21 is disposed has the L-shaped cutout 11*a* and the semicircular recessed step portion 11*b* covered and forms a cylindrical shape as a whole. Note that in FIG. 1, a portion 2*b* corresponding to the L-shaped cutout 11*a* of the second base material 2 and a portion 2*a* corresponding to the semicircular recessed step portion 11*b* are shown by being separated for convenience of illustration, but in reality, the portion 2*a* and the portion 2*b* are integrally molded.

The surface including a non-planar surface, of the second resin molded product 21 is irradiated with laser light to perform patterning and activation of the metal catalyst, electroless plating is applied to metalize only an activated portion (for example, provide nickel plating on copper plating), to form a second metal pattern 22. The second metal pattern 22 in the present embodiment is configured as a ground plane (GND plane) that shields the first metal patterns 12, 13, and 14.

The second metal pattern 22 forming a planar shape is formed to overlap at least part of the first metal patterns 12, 13, and 14 with the second resin molded product 21 between the second metal pattern 22 and the at least part of the first metal patterns 12, 13, and 14.

Specifically, the second metal pattern 22 is provided to have a width overlapping all wirings of the first metal patterns 12, 13, and 14 with the second resin molded product 21 between the second metal pattern 22 and all the wirings of the first metal patterns 12, 13 and 14 in a width direction of the wirings of the first metal patterns 12, 13, and 14 (in the example of the present embodiment, a circumferential direction of the electronic component holding member M1 forming the cylindrical shape).

The second metal pattern 22 is provided to have a length overlapping at least part of the first metal patterns 12, 13, and 14 with the second resin molded product 21 between the second metal pattern 22 and the at least part of the first metal patterns 12, 13, and 14, in the wiring direction of the first metal patterns 12, 13, and 14 (in the example of the present embodiment, an axial direction of the electronic component holding member M1 forming the cylindrical shape).

Figure 9:
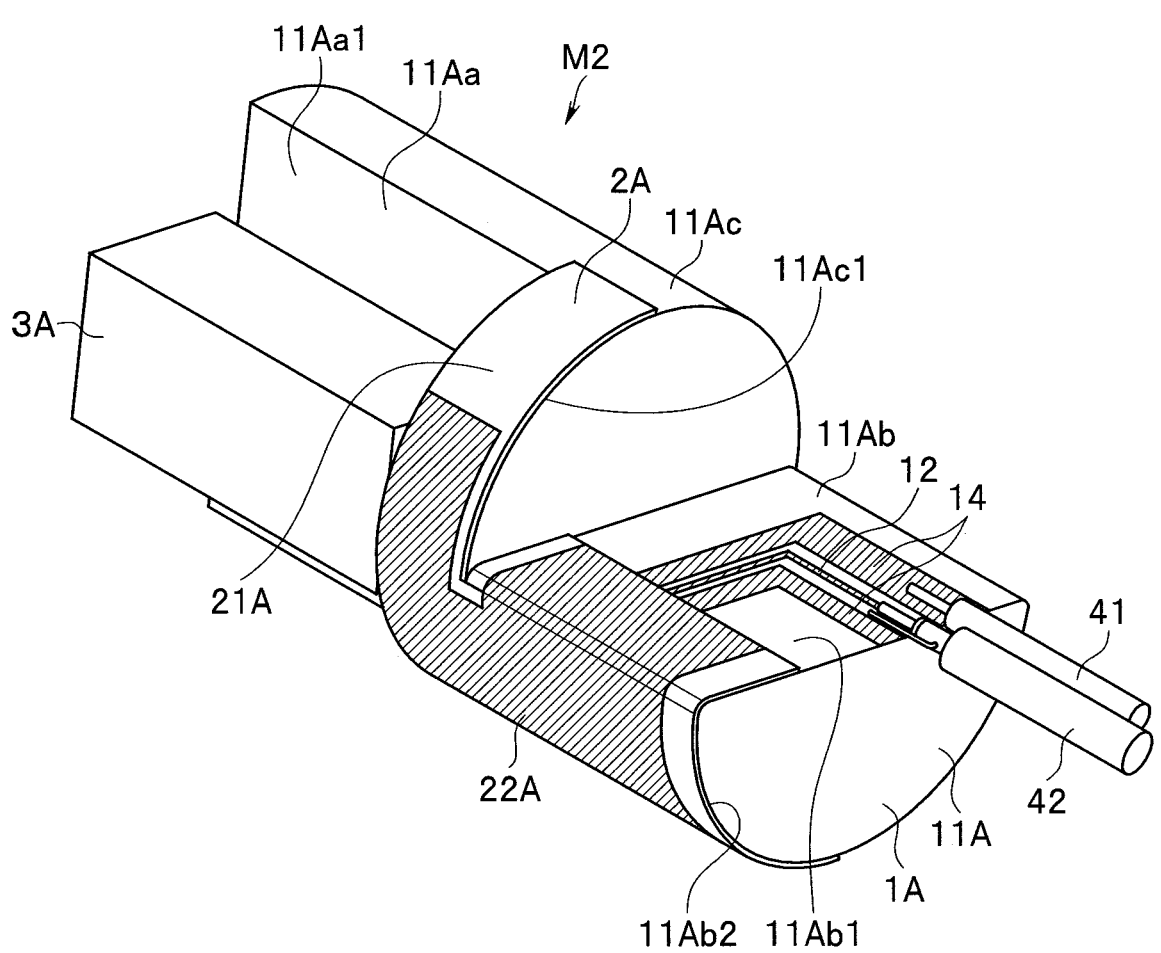
FIG. 9 is a perspective view showing a configuration in which a cable is connected to the electronic component holding member of the above-described second embodiment.
Figure 10:
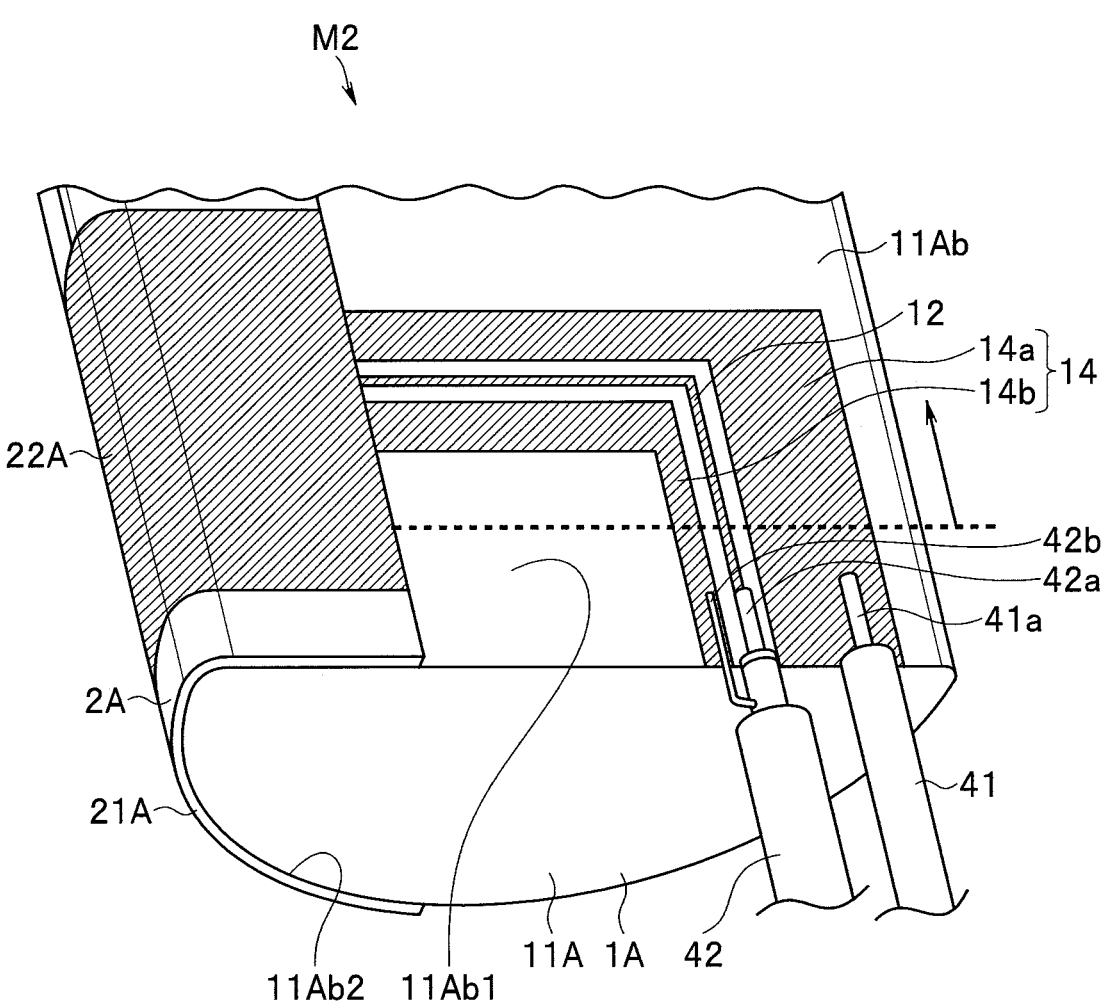
FIG. 10 is a partially enlarged perspective view showing a cable connection portion in the electronic component holding member of the above-described second embodiment.

In other words, as shown in FIG. 2, for example, the second metal pattern 22 may be formed so as not to overlap the end portions on the proximal end side of the first metal patterns 12, 13, and 14 so that a signal cable or the like can be connected to the end portions of the first metal patterns 12, 13, and 14 (see also FIG. 9, FIG. 10 and the like).

Alternatively, the second metal pattern 22 may be formed to overlap all the first metal patterns 12, 13, and 14 if the first metal patterns 12, 13, and 14, and the signal cable or the like are connected by a separate connector or the like.

Thus, the second base material 2 has the second resin molded product 21 and the second metal pattern 22.

The grounding pattern 14 and the second metal pattern 22 are connected to each other by grounding wiring 23. In a configuration example shown in FIG. 2, the grounding wiring 23 is formed on the surface of the second resin molded product 21 as a part of the second metal pattern 22, and integrated with the second base material 2. The grounding wiring 23 connects the second metal pattern 22 and the grounding pattern 14 on different layers by plating being applied to overlap the grounding pattern 14 when the second metal pattern 22 is formed.

However, the grounding wiring 23 is not limited to the above configuration, and may be configured as soldering, or may be configured as wiring. Accordingly, the grounding wiring 23 may be separated from the second base material 2.

Figure 3:
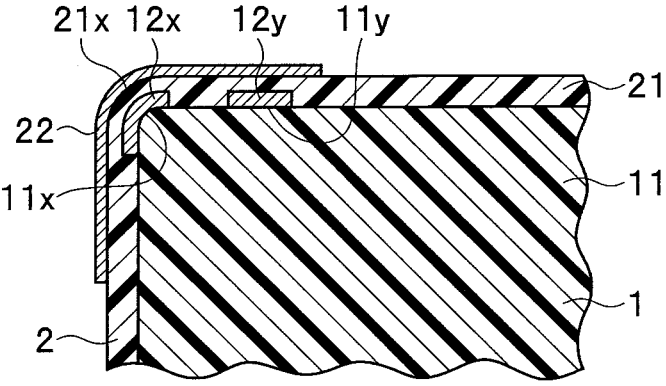
FIG. 3 is a sectional view showing an example of a configuration in which wiring is provided at a corner of the first base material, in the above-described first embodiment.

FIG. 3 is a sectional view showing an example of a configuration in which wiring is provided at a corner 11*x* of the first base material 1.

A metal pattern 12*x* is provided at the corner 11*x* of the first resin molded product 11, and a metal pattern 12*y* is provided at a planar surface portion 11*y* of the first resin molded product 11, in the first base material 1. The metal pattern 12*x* and the metal pattern 12*y* on the first resin molded product 11 are simultaneously formed by using an MID technique once. Thus, by using an MID technique, it is possible to provide the metal pattern 12*x* at the corner 11*x*, which is difficult in a conventional printed wiring board.

By using a second MID technique, the second base material 2 having the second resin molded product 21 and the second metal pattern 22 is formed on the first base material 1. The second metal pattern 22 is formed on the surface of the second resin molded product 21 including the corner 21*x* so as to overlap the metal pattern 12*x* and the metal pattern 12*y* with the second resin molded product 21 between the second metal pattern 22, and the metal pattern 12*x* and the metal pattern 12*y*.

The metal pattern 12*x* and the second metal pattern 22 that face each other with the second resin molded product 21 between the metal pattern 12*x* and the second metal pattern 22 configure a first capacitor, and the metal pattern 12*y* and the second metal pattern 22 that face each other with the second resin molded product 21 between the metal pattern 12*y* and the second metal pattern 22 configure a second capacitor.

It is possible to control a capacitance of the first capacitor by adjusting a width in FIG. 3 of the metal pattern 12*x* (area of the metal pattern 12*x* when viewed three-dimensionally), and a thickness of the second resin molded product 21 (distance between the metal pattern 12*x* and the second metal pattern 22) by an MID technique.

Likewise, it is possible to control a capacitance of the second capacitor by adjusting the width in FIG. 3 of the metal pattern 12*y* (area of the metal pattern 12*y* when viewed three-dimensionally), and a thickness of the second resin molded product 21 (distance between the metal pattern 12*y* and the second metal pattern 22) by an MID technique.

Note that the thickness of the second resin molded product 21 corresponds to a thickness of a portion 2*a* corresponding to the semicircular recessed step portion 11*b* of the second base material 2 in FIG. 1 and FIG. 2. At this time, by further adjusting a relative dielectric constant of the resin material used for the second resin molded product 21, it is possible to control the capacitances of the first capacitor and the second capacitor in a wider adjustment width.

Thus, the electronic component holding member M1 formed by the two-stage MID can perform impedance control of wiring (wiring by the metal pattern 12*x* provided at the corner 11*x*, for example) provided on a portion other than the planar surface (curved surface or the like) on a three-dimensional structure, which cannot be performed in the conventional printed wiring board, and cannot be performed by a one-stage MID, either. Accordingly, it is possible to control transmission characteristics of the signal and suppress deterioration of the signal.

The configuration of providing the wiring at the corner 11*x* as shown in FIG. 3, and the technique of the impedance control are applied to the image pickup module 3 as shown in FIG. 1 and FIG. 2, as appropriate.

Figure 4:
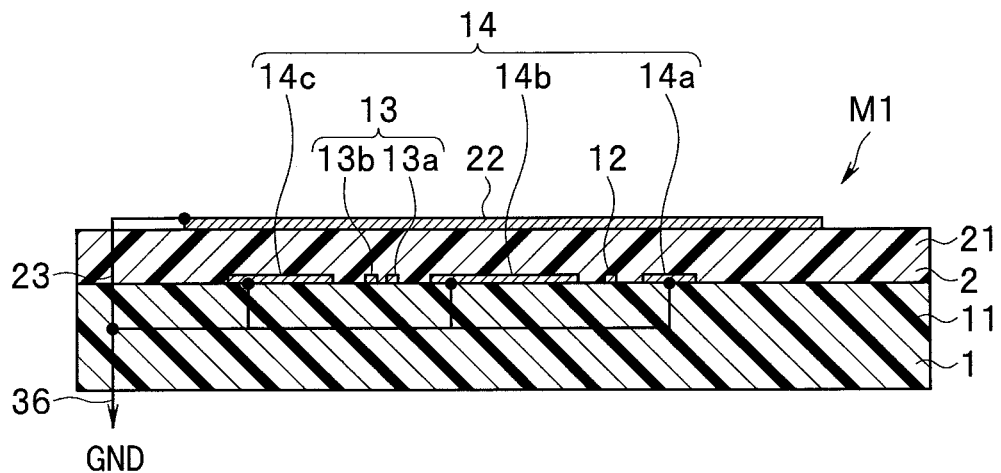
FIG. 4 is a view schematically showing a configuration in which a grounding pattern is connected to a DC power supply line including a ground, in the above-described first embodiment.

FIG. 4 is a view schematically showing a configuration of connecting the grounding pattern 14 to a DC power supply line 36 including a ground (GND). The electronic component holding member M1 forms a cylindrical shape as shown in FIG. 2, but is planarly developed and schematically shown in FIG. 4.

The grounding pattern 14 and the second metal pattern 22 are connected by the grounding wiring 23 as described above, and further connected to the DC power supply line 36 including the ground (GND).

The grounding patterns 14a and 14b are provided with the first metal pattern 12 between the grounding patterns 14a and 14b, on the surface of the first resin molded product 11. The grounding patterns 14b and 14c are provided with the first metal pattern 13 between the grounding patterns 14b and 14c, on the surface of the first resin molded product 11. Accordingly, crosstalk between a first signal transmitted through the first metal pattern 12 and a second signal transmitted through the first metal pattern 13 is suppressed.

The second metal pattern 22 is formed to overlap the first metal patterns 12, 13, and 14 with the second resin molded product 21 between the second metal pattern 22 and the first metal patterns 12, 13, and 14. Since the first signal transmitted through the first metal pattern 12, and the second signal transmitted through the first metal pattern 13 are capacitively coupled to the second metal pattern 22 connected to the ground or the like and propagated, radiated noise from the first metal pattern 12 and the first metal pattern 13 decreases.

The first signal transmitted through the first metal pattern 12, and the second signal transmitted through the first metal pattern 13 have higher resistance to noise of external factors, that is, higher immunity. Thus, the signals can be transmitted at a high clock to increase the amount of information transmitted per unit time, and thereby high-speed transmission of the signals is enabled.

The electronic component holding member M1 on which the image pickup module 3 as described above is installed is suitable for a distal end portion 52a of an endoscope 51 (see FIG. 14), for example.

According to the first embodiment as above, the first metal patterns 12, 13, and 14 are formed on the surface including the non-planar surface of the first resin molded product 11, the second resin molded product 21 is disposed on the first base material 1, the second metal pattern 22 is formed on the surface including the non-planar surface of the second resin molded product 21 so as to overlap at least part of the first metal patterns 12, 13, and 14, and the grounding pattern 14 and the second metal pattern 22 are connected by the grounding wiring 23, whereby the three-dimensional electronic component holding member M1 that is resistant to noise and capable of high-speed transmission of signals is obtained.

Immunity can be made higher if the second metal pattern 22 is overlaid on all the first metal patterns 12, 13, and 14.

When the grounding wiring 23 is formed on the surface of the second resin molded product 21 as a part of the second metal pattern 22 and integrated with the second base material 2, a separate wiring connection process is not required, and manufacturing cost can be reduced.

By adopting the image pickup module 3 as the electronic component installed in the electronic component holding member M1, the compact electronic component holding member M1 that is capable of high-speed transmission of signals, resistant to noise, and suitable for the image pickup module 3 is obtained.

Second Embodiment

Figure 5:
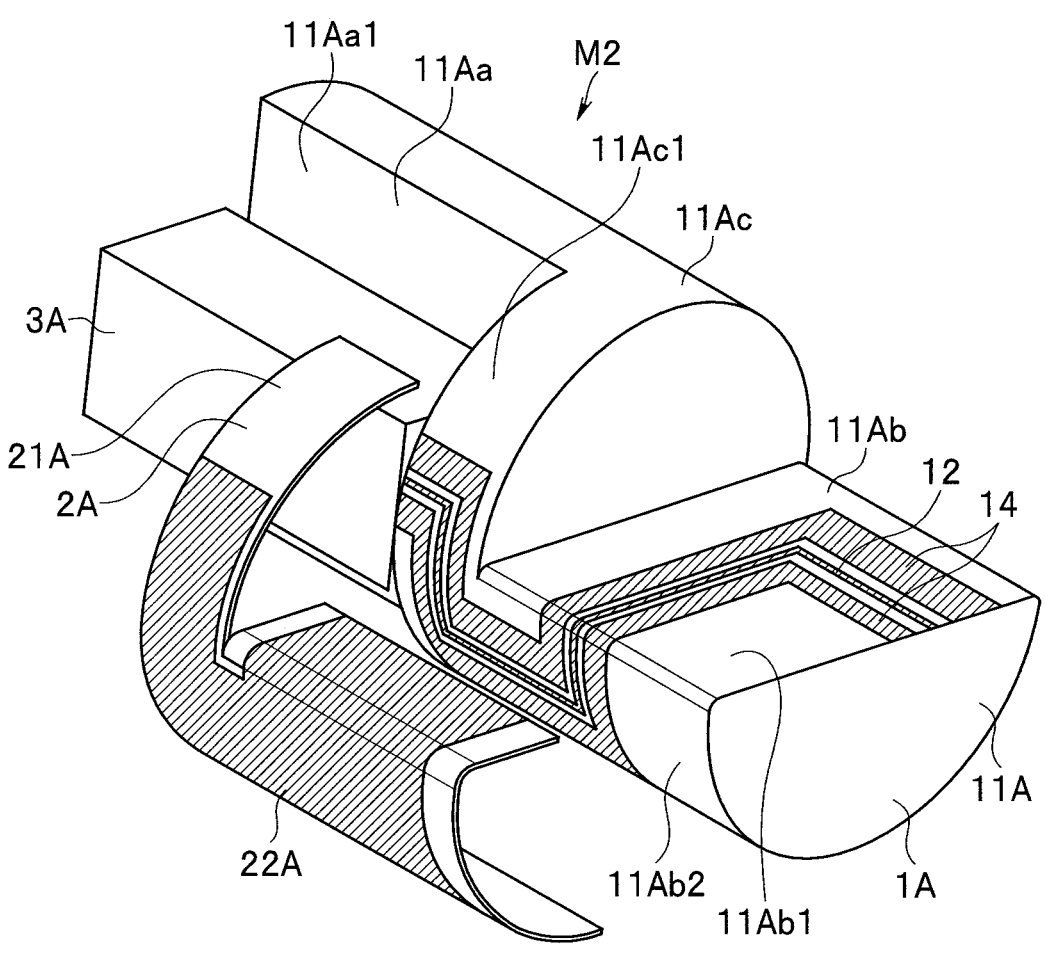
FIG. 5 is a perspective view showing a first base material and a second base material that are disassembled in an electronic component holding member of a second embodiment of the present invention.
Figure 6:
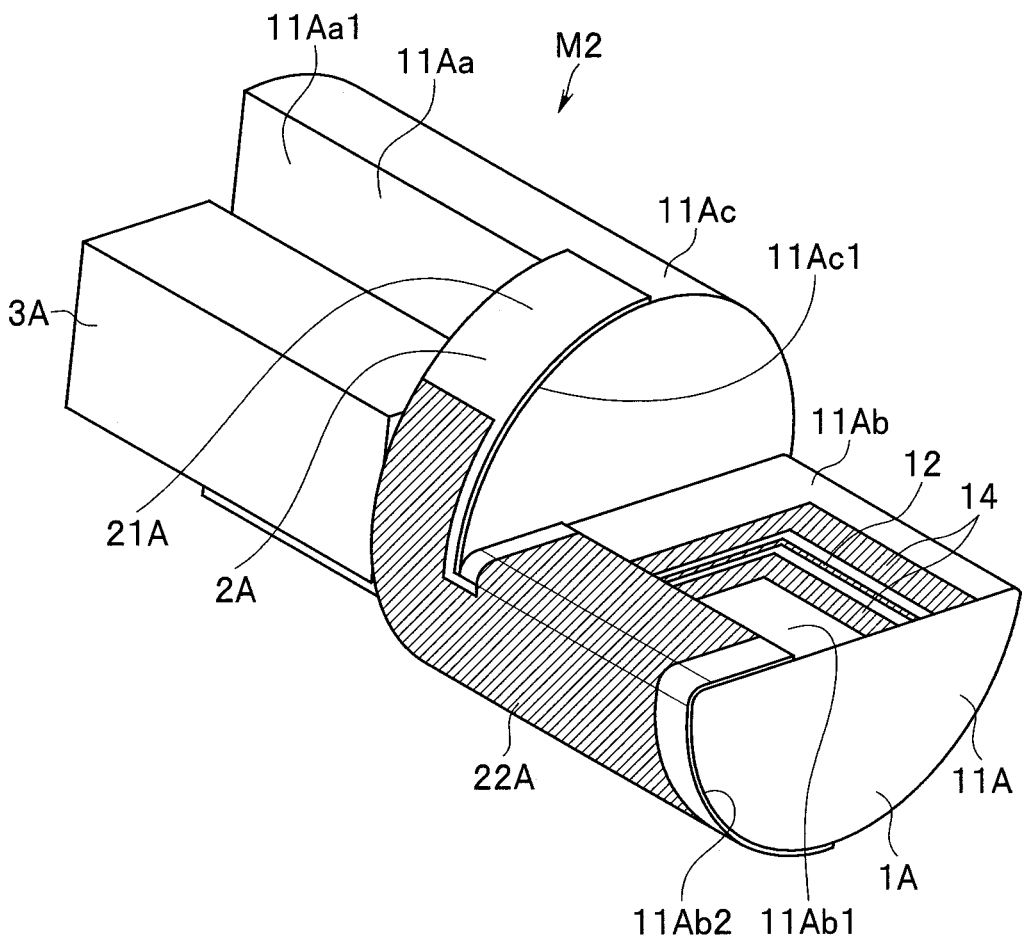
FIG. 6 is a perspective view showing the electronic component holding member of the above-described second embodiment.

FIG. 5 to FIG. 10 show a second embodiment of the present invention. FIG. 5 is a perspective view showing a first base material 1A and a second base material 2A that are disassembled in an electronic component holding member M2. FIG. 6 is a perspective view showing the electronic component holding member M2. In the second embodiment, same parts as the parts of the aforementioned first embodiment are assigned with same reference signs to omit explanation as appropriate, and only different points are mainly described.

The electronic component holding member M2 incudes the first base material 1A and the second base material 2A that are formed by a two-stage MID technique, and the second base material 2A is disposed on the first base material 1A. The electronic component holding member M2 of the present embodiment differs in shape from the electronic component holding member M1 of the first embodiment.

The first base material 1A has an electronic component, a first resin molded product 11A holding the electronic component, and a first metal pattern formed on a surface including a non-planar surface of the first resin molded product 11A.

The first resin molded product 11A is formed into a three-dimensional shape by injection molding and has a first semi-cylindrical cutout 11Aa for accommodating an image pickup module 3A (image pickup unit), a disk-shaped portion 11Ac formed on a proximal end side of the first semi-cylindrical cutout 11Aa. and a second semi-cylindrical cutout 11Ab formed on a proximal end side of the disk-shaped portion 11Ac. The first semi-cylindrical cutout 11Aa has a shape obtained by cutting out, for example, a left half of a cylinder, and the second semi-cylindrical cutout 11Ab has a shape obtained by cutting out, for example, an upper half of a cylinder. A cutout planar surface 11Aa1 parallel to an axial direction of the first semi-cylindrical cutout 11Aa. and a cutout planar surface 11Ab1 parallel to an axial direction of the second semi-cylindrical cutout 11Ab are orthogonal to each other, for example.

On the first semi-cylindrical cutout 11Aa, an image pickup module 3A (electronic component) including an image pickup device and an image pickup optical system is installed. The image pickup module 3A of the present embodiment may be of a front-view type, but may be of a side-view type including a reflective optical system, for example.

On a surface of the first resin molded product 11A, a first metal pattern electrically connected to the image pickup module 3A is formed. Note that in the present embodiment, which is more simplified than the first embodiment, illustration of a signal pattern 13 is omitted, and a signal pattern 12 and a grounding pattern 14 are illustrated as the first metal patterns, but it goes without saying that the signal pattern 13 may be provided. Hereinafter, the signal pattern 12 and the grounding pattern 14 will be collectively referred to as first metal patterns 12 and 14 as appropriate.

The first metal patterns 12 and 14 are formed from a portion of a land (not illustrated) on which the image pickup module 3A is installed, of the first semi-cylindrical cutout 11Aa to the cutout planar surface 11Ab1 of the second semi-cylindrical cutout 11Ab via a circumferential surface 11Ac1 of the disk-shaped portion 11Ac, and a circumferential surface 11Ab2 of the second semi-cylindrical cutout 11Ab.

The second base material 2A has a second resin molded product 21A and a second metal pattern 22A.

The second resin molded product 21A is formed into a plate shape forming a curved surface by injection molding, and has a three-dimensional shape that covers portions of the first metal patterns 12 and 14 formed on the circumferential surface 11Ac1 of the disk-shaped portion 11Ac, portions of the first metal patterns 12 and 14 formed on the circumferential surface 11Ab2 of the second semi-cylindrical cutout 11Ab, and at least part of the first metal patterns 12 and 14 formed on the cutout planar surface 11Ab1 of the second semi-cylindrical cutout 11Ab.

On an outer surface of the second resin molded product 21A, the second metal pattern 22A is formed to overlap the first metal patterns 12 and 14 covered with the second resin molded product 21A. The second metal pattern 22A is configured as a ground plane that shields at least part of the first metal patterns 12 and 14.

Figure 7:
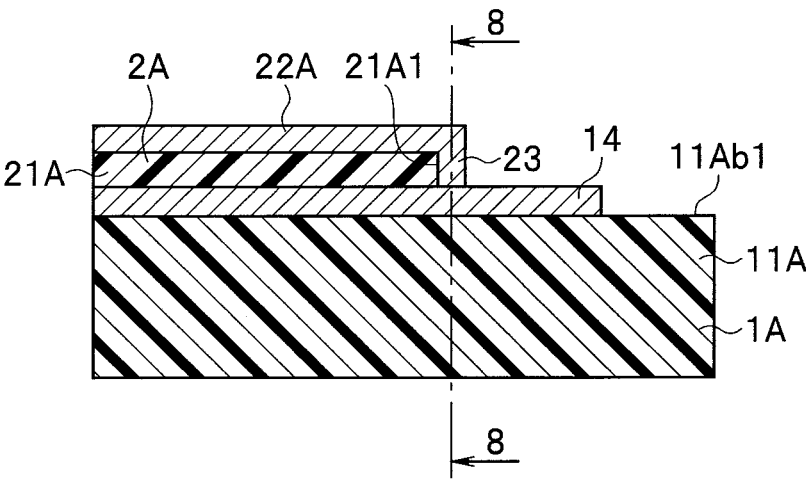
FIG. 7 is a sectional view taken along line 7-7 in FIG. 8, and schematically showing a configuration of grounding wiring connecting a grounding pattern and a second metal pattern, in the electronic component holding member of the above-described second embodiment.
Figure 8:
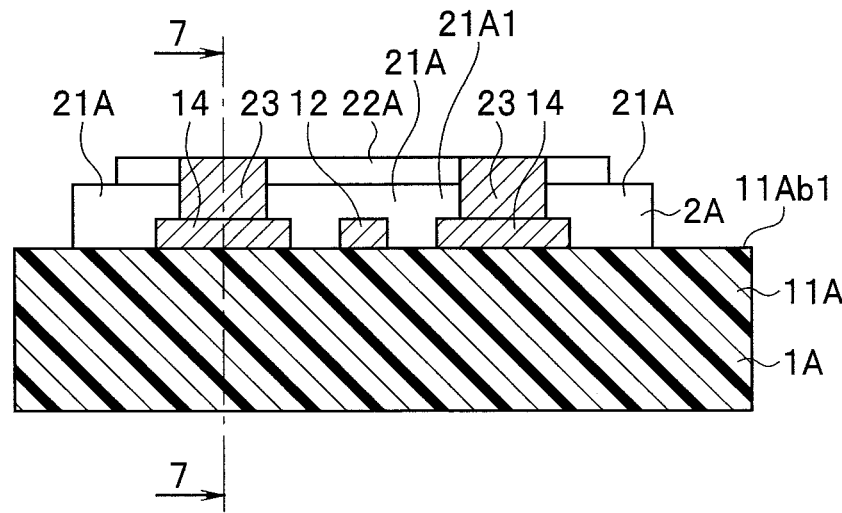
FIG. 8 is a sectional view taken along line 8-8 in FIG. 7, and schematically showing a configuration of the grounding wiring connecting the grounding pattern and the second metal pattern in the electronic component holding member of the above-described second embodiment.

FIG. 7 is a sectional view taken along line 7-7 in FIG. 8, which schematically shows a configuration of the grounding wiring 23 that connects the grounding pattern 14 and the second metal pattern 22A, in the electronic component holding member M2. FIG. 8 is a sectional view taken along line 8-8 in FIG. 7, which schematically shows the configuration of the grounding wiring 23 that connects the grounding pattern 14 and the second metal pattern 22A, in the electronic component holding member M2.

The grounding pattern 14 and the second metal pattern 22A are connected to each other by the grounding wiring 23. In configuration examples shown in FIG. 7 and FIG. 8, the grounding wiring 23 is formed on a side surface 21A1 in a thickness direction of the second resin molded product 21A as a part of the second metal pattern 22A, and integrated with the second base material 2A. The grounding wiring 23 connects the second metal pattern 22A and the grounding pattern 14 on different layers by plating being applied to overlap the grounding pattern 14 when the second metal pattern 22A is formed. However, as mentioned in the first embodiment, the grounding wiring 23 may be configured as soldering, or configured as wiring.

FIG. 9 is a perspective view showing a configuration in which a cable is connected to the electronic component holding member M2. FIG. 10 is a partially enlarged perspective view showing a cable connection portion in the electronic component holding member M2.

The signal pattern 12 and the grounding pattern 14 reach the cutout planar surface 11Ab1 from the circumferential surface 11Ab2 on the surface of the second semi-cylindrical cutout 11Ab, are placed in a width direction of the cutout planar surface 11Ab1, and thereafter folded in the axial direction to reach an end edge in the axial direction of the cutout planar surface 11Ab1 of the second semi-cylindrical cutout 11Ab.

The grounding pattern 14 has, for example, a grounding pattern 14a having a thick width, and a grounding pattern 14b having a width thinner than the grounding pattern 14a but thicker than the signal pattern 12. The signal pattern 12 is sandwiched by the grounding pattern 14a and the grounding pattern 14b on the respective surfaces on a wiring path, that is, on the circumferential surface 11Ac1, the circumferential surface 11Ab2, and the cutout planar surface 11Ab1.

A conducting wire 41a of ground wiring 41 configured by a single wire is electrically connected to an end edge portion in the axial direction of the grounding pattern 14a by soldering, for example.

A core wire 42a (inner conductor) of a coaxial cable 42 is electrically connected to an end edge portion in the axial direction of the signal pattern 12 by soldering, for example. A shielding wire 42b (external conductor) of the coaxial cable 42 is electrically connected to an end edge portion in the axial direction of the grounding pattern 14b by soldering, for example.

Using the single-wire ground wiring 41 has an advantage of being able to lower impedance and stabilize a ground potential more than using only the shielding wire 42b of the coaxial cable 42. In the configuration of the present embodiment, the shielding wire 42b is connected to the ground wiring 41 via the grounding pattern 14b, the grounding wiring 23, the second metal pattern 22A, the grounding wiring 23, and the grounding pattern 14a Therefore, there is an advantage that a ground potential of the shielding wire 42b is also stabilized. The ground wiring 41 and the shielding wire 42b configure the DC power supply line 36 shown in FIG. 4.

The electronic component holding member M2 in which the image pickup module 3A is installed as described above is suitable for the distal end portion 52a of the endoscope 51 (see FIG. 14), for example. When the electronic component holding member M2 is applied to an endoscope system 5 shown in FIG. 14, the ground wiring 41 and the coaxial cable 42 are integrated into one as a signal cable 40 and is connected to a processor 57 configured to perform signal processing, via insides of an insertion portion 52, an operation portion 53 and a universal cord 54 of the endoscope 51 (see FIG. 14).

Note that FIG. 5, FIG. 6, FIG. 9, and FIG. 10 each illustrate a state in which the second base material 2A covers a part in the width direction of the cutout planar surface 11Ab1 of the second semi-cylindrical cutout 11Ab, and this is to make it easy to understand shapes of the portions of the first metal patterns 12 and 14 which are folded in the axial direction from the width direction. The second base material 2A is preferably configured so that the second resin molded product 21A and the second metal pattern 22A cover the first metal patterns 12 and 14 up to a portion shown by a dotted line in FIG. 10 (portion except for portions where the ground wiring 41 and the coaxial cable 42 are soldered).

According to the second embodiment as above, it is possible to obtain the three-dimensional electronic component holding member M2 that can exhibit a substantially similar effect to the aforementioned first embodiment, is resistant to noise, capable of high-speed transmission of signals, and has the different configuration from the configuration of the electronic component holding member M1 of the first embodiment mentioned above.

Thus, by using a two-stage MID technique, it is possible to form the first metal patterns on each of first base materials having various three-dimensional shapes, and dispose the second base material having the second metal pattern, on each of the first base materials.

Third Embodiment

Figure 11:
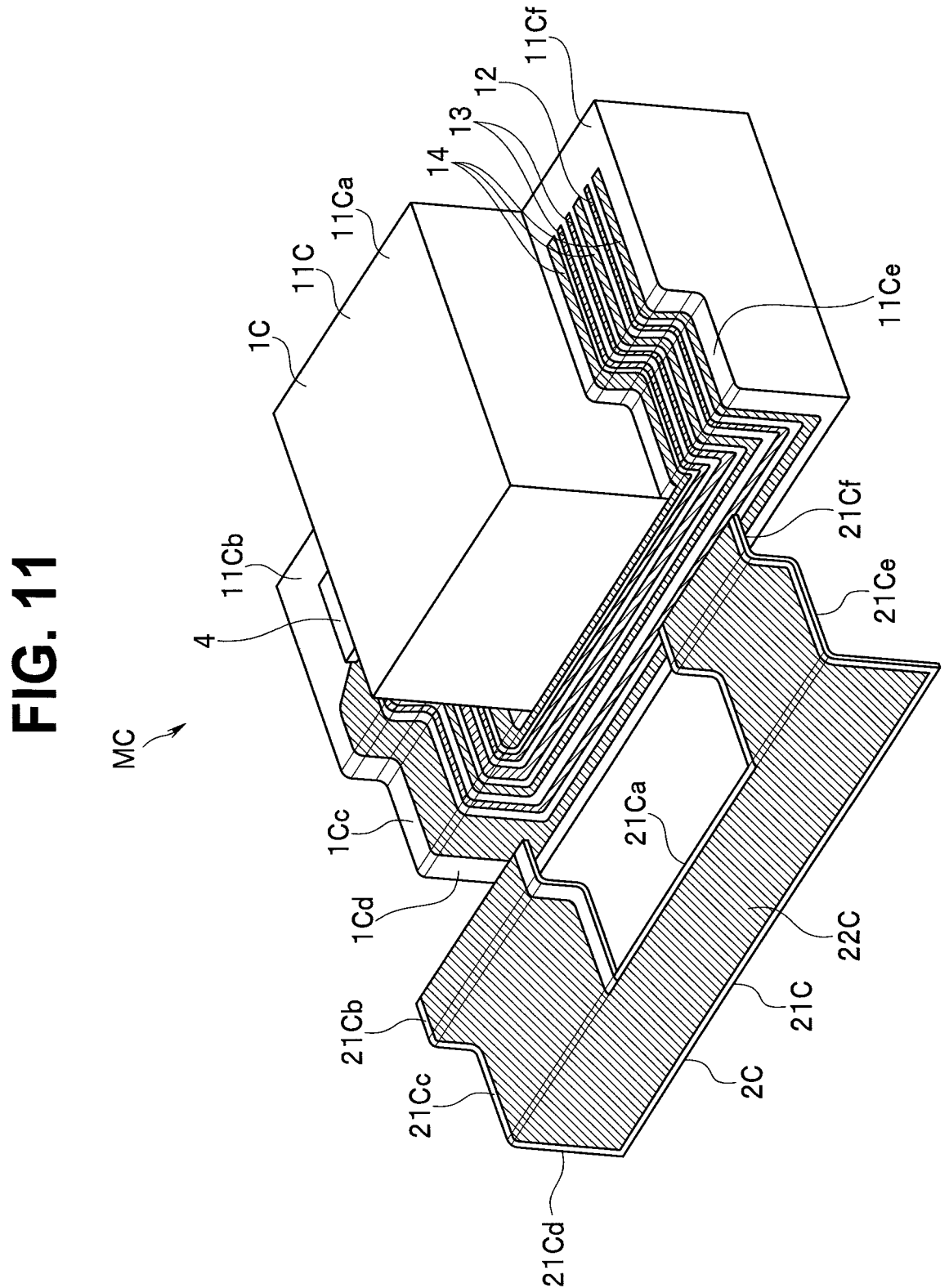
FIG. 11 is a perspective view showing a first base material and a second base material that are disassembled in an electronic component holding member of a third embodiment of the present invention.
Figure 12:
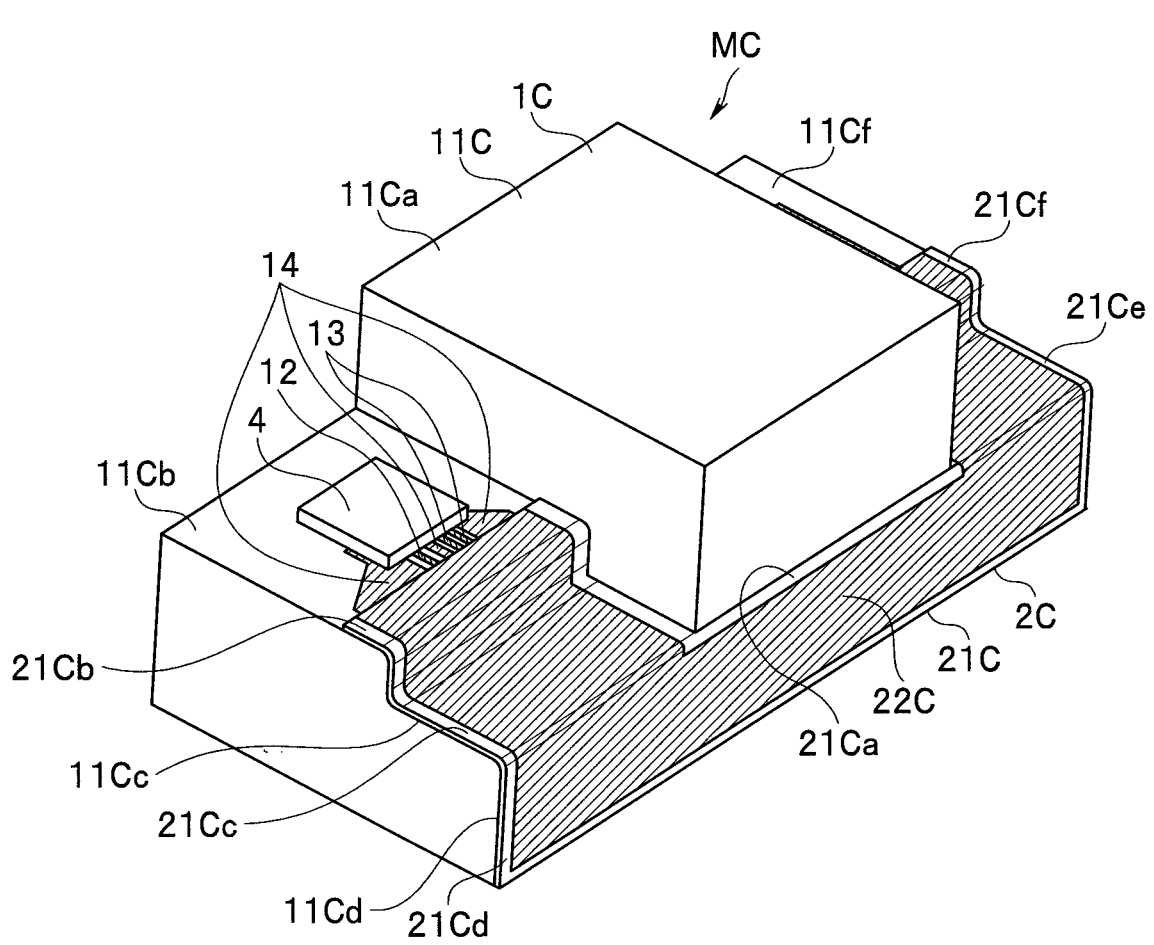
FIG. 12 is a perspective view showing the electronic component holding member of the above-described third embodiment.

FIG. 11 and FIG. 12 show a third embodiment of the present invention. FIG. 11 is a perspective view showing a first base material 1C and a second base material 2C that are disassembled in an electronic component holding member MC. FIG. 12 is a perspective view showing the electronic component holding member MC. In the third embodiment, same parts as the parts of the aforementioned first and second embodiments are assigned with same reference signs to omit explanation as appropriate, and only different points are mainly described.

In the electronic component holding member MC of the present embodiment, an IC (integrated circuit) 4 such as a CPU (central processing unit), an MCU (micro controller unit), a GPU (graphics processing unit), a RAM (random access memory), and a ROM (read only memory) is installed as an electronic component, instead of the image pickup modules 3 and 3A of the aforementioned embodiments. The electronic component holding member MC can also be installed in the operation portion 53 of the endoscope 51 shown in FIG. 14, for example, but is not limited to this and can be installed in portable communication equipment and various other electronic devices.

The electronic component holding member MC includes a first base material IC and a second base material 2C that are formed by a two-stage MID technique, and the second base material 2C is disposed on the first base material 1C.

The first base material 1C has the IC4 that is an electronic component, a first resin molded product 11C holding the IC4, and a first metal pattern formed on a surface including a non-planar surface, of the first resin molded product 11C.

The first resin molded product 11C is formed into a three-dimensional shape by injection molding, and has a rectangular convex portion 11Ca, a first shoulder portion 11Cb, a first lower step portion 11Cc, a side surface portion 11Cd, a second lower step portion 11Ce, and a second shoulder portion 11Cf.

The rectangular convex portion 11Ca is a rectangular part protruded from an upper surface of the first resin molded product 11C.

The first shoulder portion 11Cb and the second shoulder portion 11Cf are planar parts that are provided on both sides of the rectangular convex portion 11Ca and are lower than the rectangular convex portion 11Ca.

The first lower step portion 11Cc and the second lower step portion 11Ce are stepped parts including step side surfaces perpendicular to the first shoulder portion 11Cb and the second shoulder portion 11Cf respectively, and step planar surfaces that are parallel to and one-step lower than the first shoulder portion 11Cb and the second shoulder portion 11Cf respectively.

The side surface portion 11Cd is a part of a side surface connecting the first lower step portion 11Cc and the second lower step portion 11Ce on a side surface on a lower side from the first lower step portion 11Cc, the rectangular convex portion 11Ca, and the second lower step portion 11Ce.

The first metal pattern includes, for example, a signal pattern 12 of a single wire, a signal patterns 13 made up of a pair of wires, and a grounding pattern 14.

The first metal patterns 12, 13, and 14 are provided with a land formed on the first shoulder portion 11Cb and are provided to extend from the land by wirings extending to the first lower step portion 11Cc, the side surface portion 11Cd, the second lower step portion 11Ce, and the second shoulder portion 11Cf. The IC4 is installed on the land of the first shoulder portion 11Cb.

The second base material 2C has a second resin molded product 21C and a second metal pattern 22C.

The second resin molded product 21C is formed by injection molding on at least part of the first metal patterns 12, 13, and 14 provided on the first shoulder portion 11Cb, the first metal patterns 12, 13, and 14 provided on the first lower step portion 11Cc, the side surface portion 11Cd, and the second lower step portion 11Ce, and at least part of the first metal patterns 12, 13, and 14 provided on the second shoulder portion 11Cf.

Accordingly, the second resin molded product 21C has a first part 21Cb disposed on the first shoulder portion 11Cb, a second part 21Cc disposed on the first lower step portion 11Cc, a third part 21Cd disposed on the side surface portion 11Cd, a fourth part 21Ce disposed on the second lower step portion 11Ce, and a fifth part 21Cf disposed on the second shoulder portion 11Cf.

The second metal pattern 22C is formed on surfaces of the first part 21Cb to the fifth part 21Cf in the second resin molded product 21C so as to overlap the first metal patterns 12 and 14 with the second resin molded product 21C between the second metal pattern 22C and the first metal patterns 12 and 14.

According to the third embodiment as above, it is possible to obtain the three-dimensional electronic component holding member MC that can exhibit substantially same effects as the effects of the aforementioned first and second embodiments, holds an electronic component other than the image pickup module, is resistant to noise, and capable of high-speed transmission of signals.

Fourth Embodiment

Figure 13:
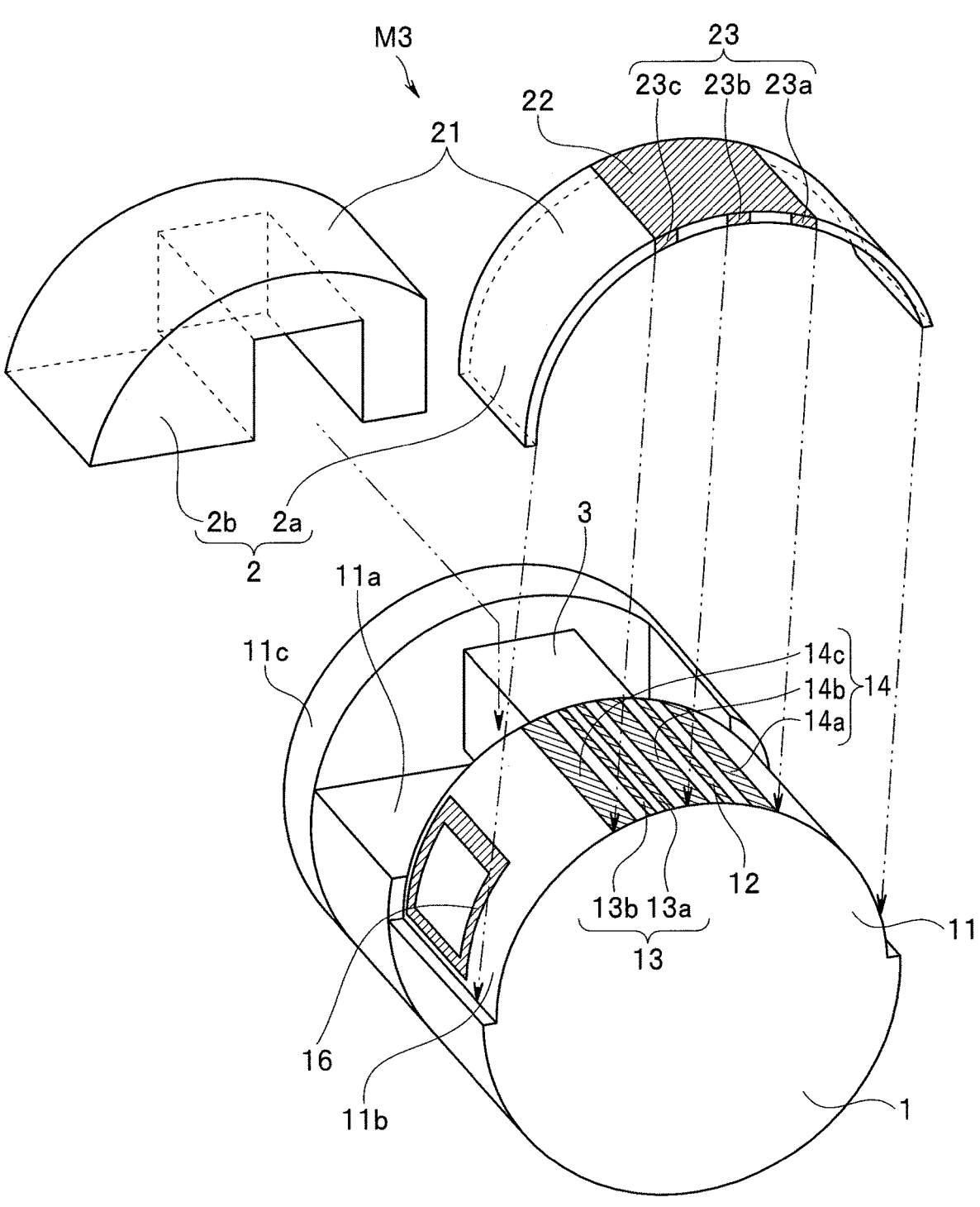
FIG. 13 is an exploded perspective view showing a configuration example in which a bonding metal pattern for bonding to a second base material is provided on a first base material, in a fourth embodiment of the present invention.

FIG. 13 shows a fourth embodiment of the present invention and is an exploded perspective view showing a configuration example in which a bonding metal pattern 16 for bonding to a second base material 2 is provided on a first base material 1. In the fourth embodiment, same parts as the parts of the aforementioned first to third embodiments are assigned with same reference signs to omit explanation as appropriate, and only different points are mainly described.

An electronic component holding member M3 of the present embodiment is basically configured similarly to the electronic component holding member M1 of the aforementioned first embodiment, but is further provided with the bonding metal pattern 16.

In a two-stage MID technique, when the second base material 2 is disposed by using a second MID technique on the first base material 1 formed by using the MID technique once, depending on a combination of the resin material forming the first resin molded product 11 and the resin material forming the second resin molded product 21, bonding strength of a contact interface may be weak and the contact interface may be peeled.

Thus, the first base material 1 of the present embodiment is further provided with the bonding metal pattern 16 that is not wiring, on the surface where the first metal patterns 12, 13, and 14 are not formed, of the first resin molded product 11. The bonding metal pattern 16 is a part for more firmly bonding the first base material 1 and the second base material 2 to obtain an anchor effect, by utilizing roughness and chemical properties of the metal surface.

Note that since the surface on which the first metal patterns 12, 13, and 14 are formed, of the first resin molded product 11 already has the anchor effect owing to the roughness and the chemical properties of the metal surface, the contact interface is not peeled basically.

In addition to the bonding metal pattern 16, the surface in contact with the second base material 2, of the first base material 1 may be roughened by blasting, for example, to form fine irregularities on the surface of the first base material 1 to further obtain an anchor effect. Alternatively, only roughening of the surface of the first base material 1 may be performed instead of the bonding metal pattern 16.

Note that one or both of providing a bonding metal pattern on the surface of the first resin molded product, and roughening the surface of the first base material may be applied to any of the configurations of the aforementioned first to third embodiments.

According to the fourth embodiment like this, at least one of providing the bonding metal pattern 16 on the surface of the first resin molded product 11 and roughening the surface of the first base material 1 is performed, and therefore, it is possible to increase bonding strength of the first base material 1 and the second base material 2 after realizing similar impedance control to the impedance control of the aforementioned first to third embodiments.

Figure 14:
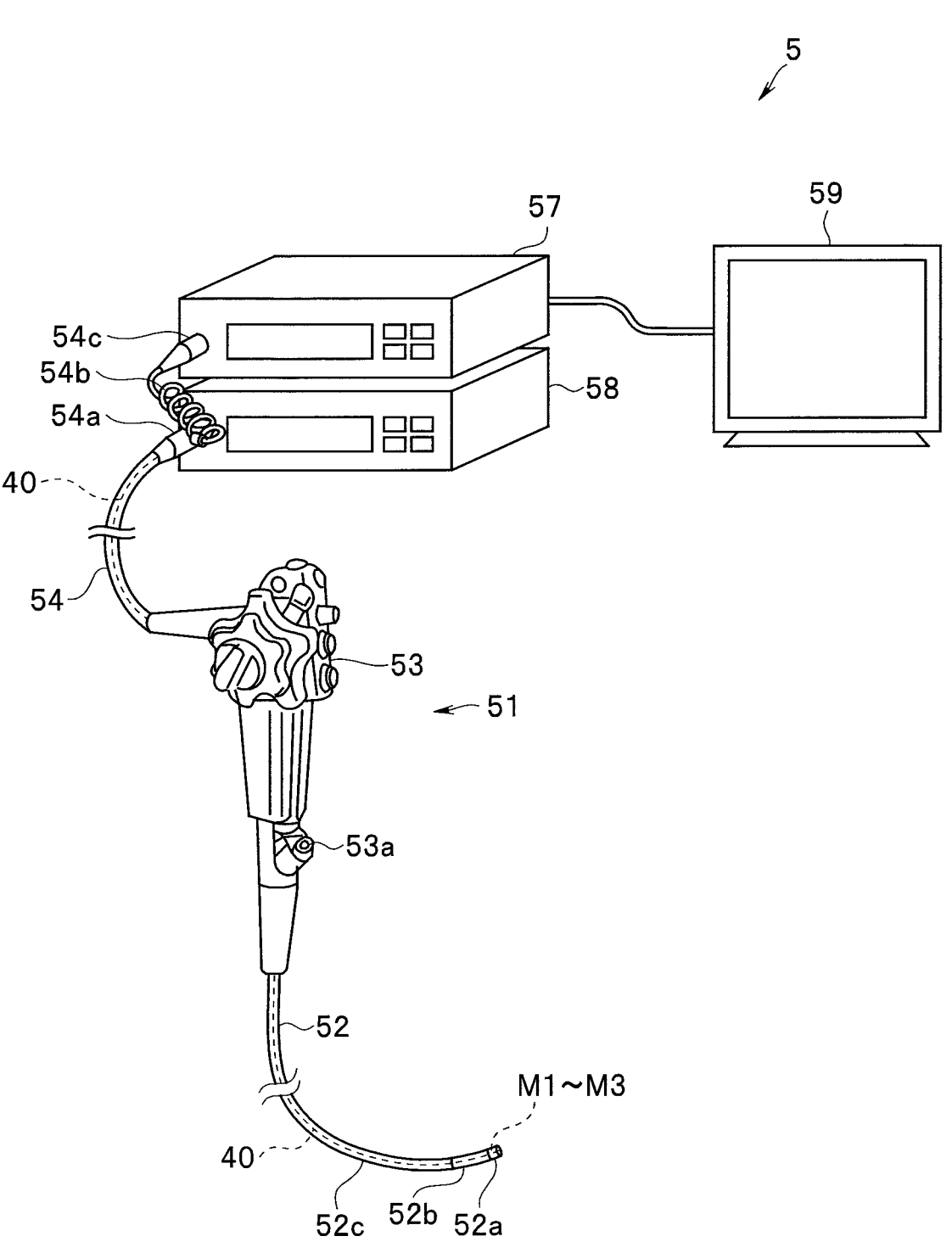
FIG. 14 is a view showing an example of an endoscope system including an endoscope equipped with the electronic component holding member of each of the above-described embodiments.

Next, FIG. 14 is a view showing an example of the endoscope system 5 including an endoscope in which each the electronic component holding members M1 to M3 and MC of the above-described respective embodiments is installed.

As shown in FIG. 14, the endoscope system 5 includes the endoscope 51, the processor 57, a light source apparatus 58, and a monitor 59.

The endoscope 51 includes the elongated insertion portion 52 configured to be inserted into a subject, the operation portion 53 connectively provided on a proximal end side of the insertion portion 52, and the universal cord 54 extending from the operation portion 53. Note that the subject to which the insertion portion 52 is inserted may be a living thing such as a person or an animal or may be a non-living thing such as a machine or a building.

In the insertion portion 52, the distal end portion 52*a*, a bending portion 52*b*, and a flexible tube portion 52*c* are connectively provided in this order from a distal end side to the proximal end side.

The endoscope 51 is configured as an electronic endoscope, and any one of the electronic component holding members M1 to M3 of the above-described respective embodiments in each of which the image pickup module is installed is placed in the distal end portion 52*a*. When the insertion portion 52 is inserted into a body cavity of a subject, the image pickup module of each of the electronic component holding members M1 to M3 picks up an image of the body cavity of the subject and outputs an image pickup signal.

The bending portion 52*b* is configured to be bendable in two directions, or four directions of up, down, left, and right, for example. The bending portion 52*b* bends by a bending operation in the operation portion 53. When the bending portion 52*b* is bent, a direction of the distal end portion 52*a* changes, and an observation direction of the image pickup module of each of the electronic component holding members M1 to M3 changes. The bending portion 52*b* is also bent to improve insertion properties of the insertion portion 52 in the subject. Note that the endoscope 51 including the bending portion 52*b* is cited as an example here, but the endoscope 51 may be of a type that does not include the bending portion 52*b*.

The flexible tube portion 52*c* is a flexible tube portion that bends according to a shape of the subject to which the insertion portion 52 is inserted. Although the flexible endoscope including the flexible tube portion 52*c* is cited as an example of the endoscope 51 here, the endoscope 51 may be a rigid endoscope including a rigid tube portion that does not bend. For example, the rigid endoscopes and the flexible endoscopes of the medical field are defined in ISO8600-1: 2015.

The operation portion 53 is connectively provided on the proximal end side of the insertion portion 52, and is a part configured to be grasped by a hand to perform various operations concerning the endoscope 51. The operation portion 53 has, for example, a bending operation lever for performing a bending operation of the bending portion 52*b*, and various operation buttons such as a gas/liquid feeding button, a suction button, and a button switch. The gas/liquid feeding button is an operation button for delivering gas or liquid via a gas/liquid feeding channel not illustrated, for example, and feeding gas/liquid to a cover glass provided at a distal end of the image pickup module from a nozzle provided at the distal end portion 52*a*. The suction button is an operation button for performing suction from a distal end portion 52*a* side via a treatment instrument channel, for example. The button switch is an operation button for mainly performing operations relating to image pickup, for example.

A treatment instrument insertion port 53*a* is provided on a distal end side of the operation portion 53. The treatment instrument insertion port 53*a* is an opening on a proximal end side of the treatment instrument channel, and the distal end portion 52*a* is provided with an opening (not illustrated) on a distal end side of the treatment instrument channel. A treatment instrument such as biopsy forceps and a high-frequency snare is inserted into the treatment instrument channel to perform treatment of the subject or the like.

The universal cord 54 is a connection cord for connecting the endoscope 51 to the light source apparatus 58 and the processor 57. A connector 54*a* is provided at an extension end of the universal cord 54. The universal cord 54 is connected to the light source apparatus 58 by using the connector 54*a*.

A coil-shaped electric cable 54*b* is extended from the connector 54*a*, and a connector 54*c* provided at an extension end of the electric cable 54*b* is connected to the processor 57.

The signal cable 40 including the ground wiring 41 and the coaxial cable 42 described above is connected to the image pickup module of each of the electronic component holding members M1 to M3 in the distal end portion 52*a*, and the signal cable 40 is connected to the processor 57 and the light source apparatus 58 via the insertion portion 52, the operation portion 53, and the universal cord 54 (including the connector 54*a*, the electric cable 54*b*, and the connector 54*c*). The processor 57 transmits a drive signal for driving the image pickup module via the signal cable 40. An image pickup signal outputted from the image pickup module is transmitted to the processor 57 via the signal cable 40.

Note that the electronic component holding member MC in which the aforementioned IC4 is installed may be provided in, for example, the operation portion 53 of the endoscope 51. In this case, the signal cable 40 is also connected to the IC4 of the electronic component holding member MC, and the IC4 is connected to the processor 57 and the light source apparatus 58.

A light guide not illustrated is provided in the insertion portion 52, the operation portion 53, and the universal cord 54 of the endoscope 51. The light guide transmits illumination light emitted from the light source apparatus 58 to an illumination optical system provided at the distal end portion 52*a* of the insertion portion 52. The illumination optical system irradiates the subject with illumination light.

The processor 57 controls the entire endoscope system 5 and performs signal processing for the image pickup signal received via the signal cable 40 to generate an image signal capable of being displayed to output the image signal to the monitor 59. The monitor 59 displays an endoscope image by the image signal outputted from the processor 57.

Note that the processor 57 and the light source apparatus 58 are not limited to being separately configured and may be integrally configured. Illumination light is not limited to the configuration in which the light source apparatus 58 emits the illumination light, but a configuration may be adopted, in which a light emitting element such as an LED is provided at the distal end portion 52*a* of the insertion portion 52, and the light emitting element emits illumination light by being supplied with electric power.

Note that the present invention is not limited to the aforementioned embodiments but can be embodied by modifying the components within the range without departing from the gist of the invention at the implementation stage.

Various aspects of the invention can be formed by the suitable combinations of the plurality of components disclosed in the above-described embodiments. For example, some components may be deleted from all the components shown in the embodiments. Furthermore, the components across the different embodiments may be combined as appropriate. Thus, it goes without saying that various modifications and applications are possible within the range without departing from the gist of the invention.

What is claimed is:

1. An electronic component holding member comprising:
a first base material including
an electronic component,
a first resin molded product configured to hold the electronic component, and
first metal patterns formed on a surface including a non-planar surface, of the first resin molded product, the first metal patterns including a signal pattern configured to perform signal transmission with the electronic component, and a grounding pattern;
a second base material including
a second resin molded product disposed on the first base material, and
a second metal pattern formed on a surface including a non-planar surface, of the second resin molded product so as to overlap at least part of the first metal patterns with the second resin molded product between the second metal pattern and the at least part of the first metal patterns; and
grounding wiring configured to connect the grounding pattern and the second metal pattern.

2. The electronic component holding member according to claim 1,
wherein the second base material is configured so that the second metal pattern overlaps all the first metal patterns.

3. The electronic component holding member according to claim 1,
wherein the grounding wiring is formed on a surface of the second resin molded product as a part of the second metal pattern and integrated with the second base material.

4. The electronic component holding member according to claim 1, wherein the first base material further includes a bonding metal pattern that is provided on a surface of the first resin molded product where the first metal patterns are not formed, and configured to bond the first base material to the second base material.

5. The electronic component holding member according to claim 1,
wherein the electronic component is an image pickup module including an image pickup device.

6. An endoscope equipped with an electronic component holding member comprising
a first base material including
an electronic component,
a first resin molded product configured to hold the electronic component, and
first metal patterns formed on a surface including a non-planar surface, of the first resin molded product, the first metal patterns including a signal pattern configured to perform signal transmission with the electronic component, and a grounding pattern,
a second base material including
a second resin molded product disposed on the first base material, and
a second metal pattern formed on a surface including a non-planar surface, of the second resin molded product so as to overlap at least part of the first metal patterns with the second resin molded product between the second metal pattern and the at least part of the first metal patterns, and
grounding wiring configured to connect the grounding pattern and the second metal pattern.

7. The endoscope according to claim 6,
wherein the second base material is configured so that the second metal pattern overlaps all the first metal patterns.

8. The endoscope according to claim 6,
wherein the grounding wiring is formed on a surface of the second resin molded product as a part of the second metal pattern and integrated with the second base material.

9. The endoscope according to claim 6, wherein the first base material further includes a bonding metal pattern that is provided on a surface of the first resin molded product where the first metal patterns are not formed, and configured to bond the first base material to the second base material.

10. The endoscope according to claim 6,
wherein the electronic component is an image pickup module including an image pickup device.

* * * * *